US008692045B2

(12) United States Patent
Qi et al.

(10) Patent No.: US 8,692,045 B2
(45) Date of Patent: Apr. 8, 2014

(54) PROCESSES FOR PRODUCING LIGHT OLEFINS

(75) Inventors: Guozhen Qi, Shanghai (CN); Siqing Zhong, Shanghai (CN); Wei Chen, Shanghai (CN); Zhinan Yu, Shanghai (CN)

(73) Assignees: China Petroleum & Chemical Corporation, Beijing (CN); Shanghai Research Institute of Petrochemical Technology, Shanghai (CN)

( * ) Notice: Subject to any disclaimer, the term of this patent is extended or adjusted under 35 U.S.C. 154(b) by 40 days.

(21) Appl. No.: 13/298,137

(22) Filed: Nov. 16, 2011

(65) Prior Publication Data

US 2012/0123179 A1    May 17, 2012

(30) Foreign Application Priority Data

Nov. 17, 2010  (CN) .......................... 2010 1 0553849

(51) Int. Cl.
*C07C 1/24* (2006.01)
(52) U.S. Cl.
USPC ........... 585/639; 585/638; 422/187; 422/139; 422/141; 422/144; 422/145; 422/146; 422/600; 422/601; 422/200; 422/201
(58) Field of Classification Search
USPC .......... 585/638, 639; 422/187, 139, 141, 144, 422/145, 146, 600, 601, 200, 201
See application file for complete search history.

(56) References Cited

U.S. PATENT DOCUMENTS 4,071,573 A * 1/1978 Owen et al. ................... 585/402
4,499,327 A   2/1985 Kaiser
6,166,282 A * 12/2000 Miller ........................... 585/638
7,195,741 B2 * 3/2007 Lattner et al. ................. 422/141
7,316,773 B2   1/2008 Zhang et al.

FOREIGN PATENT DOCUMENTS

| CN | 1438296 A | 8/2003 |
|---|---|---|
| CN | 1723262 A | 1/2006 |
| CN | 101239869 A | 8/2008 |
| CN | 101265150 A | 9/2008 |
| CN | 101333141 A | 12/2008 |
| CN | 101402538 A | 4/2009 |

OTHER PUBLICATIONS

Ye et al., "Synthesis of SAPO-34 Molecular Sieves and Their Catalytic Performances in Methanol-to-Olefins Reaction," *Journal of East China University of Science and Technology* (*Natural Science Edition*), 36(1): 6-12 (2008).

* cited by examiner

*Primary Examiner* — In Suk Bullock
*Assistant Examiner* — Sharon Pregler
(74) *Attorney, Agent, or Firm* — Finnegan, Henderson, Farabow, Garrett & Dunner LLP.

(57) ABSTRACT

A process for producing light olefins is provided. A feedstock enters a pre-reaction zone and contacts a catalyst comprising at least one silicon-aluminophosphate molecular sieve and produces a gas-phase stream; the gas-phase stream and the catalyst enter at least one riser, and the gas-phase stream and the catalyst pass from an outlet of the at least one riser and enter a gas-solid rapid separation zone; the separated gas-phase stream enters a separation section; a first portion of the separated catalyst returns to the pre-reaction zone, and a second portion is regenerated in a regenerator; wherein an inlet of the at least one riser extends into the pre-reaction zone, about 60% to about 90% of the height of the at least one riser passes through a heat exchange zone, and the outlet extends into the gas-solid rapid separation zone.

18 Claims, 2 Drawing Sheets

PROCESSES FOR PRODUCING LIGHT OLEFINS

This application claims priority under 35 U.S.C. §119 to Chinese Patent Application No. 201010553849.3, filed Nov. 17, 2010.

This disclosure relates to processes for producing light olefins.

Light olefins, for example, ethylene and propylene, are basic chemical engineering raw materials for which there is an increasing demand. Generally, ethylene and propylene are produced from petroleum. Due to limited supplies and high prices for petroleum resources, the cost of producing ethylene and propylene from petroleum is continuously increasing. Recently, techniques for preparing ethylene and propylene by converting petroleum alternatives have been developed. Substitute raw materials for producing light olefins include oxygenates such as alcohols (for example, methanol and ethanol), ethers (for example, dimethyl ether and methyl ethyl ether), and esters (for example, dimethyl carbonate and methyl formate), which can be converted from energy sources such as coal, natural gas and biomass. Some oxygenates, such as methanol, can be produced from coal or natural gas on a large scale, reaching production scales up to, for example, millions of tons. Due to the abundant supply of such oxygenates and more economically efficient techniques for light olefin production by converting petroleum alternatives, Oxygenate to Olefins processes (OTO), especially Methanol to Olefins processes (MTO), have drawn more and more attention.

Silicon-aluminophosphate molecular sieve catalysts for converting methanol to olefins have been reported, such as, wherein SAPO-34 is reportedly used as the catalyst for MTO processes. See, e.g., U.S. Pat. No. 4,499,327. The SAPO-34 catalyst reportedly has a high selectivity to light olefins and also a higher activity, and can reportedly reach a reaction time of less than 10 sec for converting methanol to light olefins and even reach the time within the reaction time range of a riser.

Techniques and reactors for converting methanol to light olefins have also been reported. See, e.g., U.S. Pat. No. 6,166,282. However, yields of light olefins could desirably be improved.

Multiple riser reactors with centralized catalyst return used for processes of converting oxide to light olefin have also been reported, such as in Chinese Patent No. CN1723262. However, yields of light olefins could desirably be improved. Moreover, it has been reported that raw material directly enters into the riser, which could generate a large temperature gradient inside the riser, which could make it difficult to remove heat from the reaction.

Therefore, from published reports, it appears that it would be desirable to improve even further the yield of light olefins.

Disclosed herein are processes for producing light olefins and exemplary apparatus for doing so. The processes are used for the production of light olefins (e.g., ethylene and propylene), and have been found, under conditions tested, to obtain desirable yields of light olefins.

In one embodiment, a process disclosed herein comprises:

contacting, in a pre-reaction zone a feedstock with a catalyst comprising at least one silicon-aluminophosphate molecular sieve to produce a gas-phase stream;

passing the gas-phase stream and the catalyst into at least one riser, passing the gas-phase stream and the catalyst through an outlet of the at least one riser into a gas-solid rapid separation zone to separate therein the gas-phase stream and the catalyst;

passing the separated gas-phase stream into a separation section;

returning a first portion of the separated catalyst to the pre-reaction zone, and regenerating a second portion of the separated catalyst in a regenerator;

wherein an inlet of the at least one riser extends into the pre-reaction zone, further wherein about 60% to about 90% of the height of the at least one riser passes through a heat exchange zone, and even further wherein the outlet of the at least one riser extends into the gas-solid rapid separation zone.

In the process disclosed herein, the at least one silicon-aluminophosphate molecular sieve can be chosen, for example, from SAPO-5, SAPO-11, SAPO-17, SAPO-18, SAPO-34, SAPO-35, SAPO-44 and SAPO-56, such as SAPO-34. The feedstock may be methanol. The pre-reaction zone may contain a dense phase and/or rapid fluidized bed. In some embodiments, the reaction conditions of the pre-reaction zone may include: a gauge pressure ranging from about 0.01 MPa to about 0.3 MPa; an average temperature ranging from about 350° C. to about 470° C.; an average carbon deposit weight fraction of the catalyst ranging from about 1.5% to about 4.5%; and a gas residence time in the pre-reaction zone ranging from about 2 sec to about 6 sec.

In some embodiments, the reaction conditions of the at least one riser may include: a gauge pressure ranging from about 0.01 MPa to about 0.3 MPa; an average temperature ranging from about 420° C. to about 530° C.; a gas residence time in the at least one riser ranging from about 0.4 sec to about 2 sec. The gas-phase residence time in the gas-solid rapid separation zone may range from about 1 sec to about 3 sec.

The portion of the at least one riser in the heat exchange zone may exchange heat with a first heat exchange medium in an indirect heat exchange manner. The first heat exchange medium may comprise, for example, water or the feedstock, such as methanol, and such as at least 80 wt %, even, at least 90 wt % methanol.

The gas-solid rapid separation zone may be located within a disengaging zone, and the upper portion of the disengaging zone may include a gas-solid cyclone separator for further gas-solid separation.

In some embodiments, the heat released in the pre-reaction zone may be removed by cooling. The cooling may be accomplished, for example, by setting up an internal cooling coiled tube to exchange heat with a second heat exchange medium. The second heat exchange medium may be for example, water.

In some embodiments, the number of the at least one riser is at least 3 and the height of the at least one riser is at least 10 m. In some embodiments, about 50% to about 80% by weight of the separated catalyst returns to the pre-reaction zone, and about 20% to about 50% by weight is regenerated in the regenerator.

As disclosed herein, the average temperature in the reaction zone is calculated as the arithmetical average number of the inlet temperature and the outlet temperature of the reaction zone.

As disclosed herein, the number of the at least one riser in certain embodiments is chosen depending upon the scale of the feedstock to be treated; for example, 3 to 8 risers are used when the scale of the feedstock to be treated is 1,800,000 ton of methanol per year.

As disclosed herein, the average carbon deposit weight fraction of the catalyst is calculated as the weight of the deposited carbon on a certain weight of the catalyst divided by that certain weight of the catalyst. The weight of the deposited carbon on the catalyst may be determined as follows: mixing the catalyst having deposited carbon thereon; then precisely weighing a certain weight of the catalyst to combust it in a high-temperature carbon analyzer; determining the weight of the carbon dioxide generated from combustion by an infrared manner and performing the calculation described above.

The at least one silicon-aluminophosphate molecular sieve used herein may be prepared by, first preparing a molecular sieve precursor, by mixing materials in a molar ratio ranging from R:(Si:Al:P):$H_2O$ being about 0.03-0.6 R:(about 0.01-0.98 Si:about 0.01-0.6 Al:about 0.01-0.6 P):about 2-500 $H_2O$, wherein R is a template agent, to form a mixed solution by crystallizing precipitates at a certain temperature (e.g. from about 100° C. to about 250° C.), for a certain period of time (e.g. from about 1 hour to about 10 hours); second, mixing the molecular sieve precursor, a phosphorus source, a silicon source, an aluminum source, a fluorine source such as hydrofluoric acid, an organic template agent and water in a certain ratio (for example, 0.03-0.6 R:0.03-0.6 F:(0.01-0.98 Si:0.01-0.6 Al:0.01-0.6 P):2-500 $H_2O$), wherein R is an organic template agent, at a temperature ranging from about 110° C. to about 260° C. for at least 0.1 h of hydrothermal crystallization to obtain SAPO molecular sieves. The prepared molecular sieves are then mixed with a binder in a certain ratio, spray-dried, and calcined to obtain the final SAPO catalyst, wherein the binder may be added in an amount ranging from about 10% to about 90% by weight of the molecular sieves.

In some embodiments, a certain proportion of at least one diluent may be optionally included in the feedstock. The at least one diluent may be chosen from light alkanes (for example, methane and ethane), CO, nitrogen, and steam. In an embodiment, light alkanes and steam are used. In another embodiment, steam is used. The volume ratio of the at least one diluent to the feedstock may be adjusted within the range from about 0.1:1 to about 10:1.

The increase of linear velocity of the reactants and the decrease of the gas-phase residence time may promote the production of light olefins with high selectivity. For MTO reactions having raw materials with relatively small molecular weights and a relatively large exotherm, there may be difficulties in heat transfer and production scale with the traditional riser reactors. In an embodiment of the process disclosed herein, the feedstock enters the pre-reaction zone first, and the pre-reaction zone is used for mixing the catalyst to be regenerated and the regenerated catalyst. A cooling means may be also set up in the pre-reaction zone. Therefore, the majority of the feedstock can be converted at a lower reaction temperature, and the generation of byproducts like CO and $H_2$ can be prevented or at least reduced. Most of the reaction heat of the MTO reaction can be removed from the pre-reaction zone. The gas-solid mixture exiting from the pre-reaction zone then enters the at least one riser: on one hand, the unconverted feedstock from the pre-reaction zone can be converted; on the other hand, the higher olefins generated in the reaction can be cracked at a higher temperature, and in the meantime, the high linear velocity in the at least one riser can reduce the possibility of secondary reactions to the main product light olefin, thus increasing the yield of light olefins. The gas-solid mixture exiting from the at least one riser then enters the gas-solid rapid separation zone to realize the rapid separation of the gas-solid mixture and further reduce the possibility of secondary reactions. Therefore, the process disclosed herein can desirably increase the yield of light olefins. For example, in certain embodiments, the yield of light olefin carbon radicals from the process disclosed herein has reached about 85.17% by weight.

An apparatus for the preparation of light olefins is also provided, comprising:
a pre-reaction zone for contacting a feedstock with a catalyst,
at least one riser,
a gas-solid rapid separation zone in flow communication with the at least one riser,
a separation section, and
a catalyst regenerator;
wherein an inlet of the at least one riser extends into the pre-reaction zone, further wherein about 60% to about 90% of the height of the at least one riser passes through a heat exchange zone, and even further wherein an outlet of the at least one riser extends into the gas-solid rapid separation zone.

In an embodiment disclosed herein, the apparatus for the preparation of light olefins is used for carrying out the process for preparing light olefins, as disclosed herein.

BRIEF DESCRIPTION OF THE DRAWINGS

In FIG. 1,
1 represents a feedstock;
2 represents a pre-reaction zone;
3 represents an inlet of the pre-reaction zone for a second heat exchange medium;
4 represents an outlet of the pre-reaction zone for the second heat exchange medium;
5 represents a distributing plate of the pre-reaction zone;
6 represents an internal cooling coiled tube of the pre-reaction zone;
7 represents a sloped regeneration tube, which follows a catalyst regenerator 21;
8 represents a recirculation tube for a catalyst to be regenerated;
9 represents an outlet of a heat exchange zone for a first heat exchange medium;
10 represents the heat exchange zone;
11 represents an inlet of the heat exchange zone for the second heat exchange medium;
12 represents an inlet for a stripping medium;
13 represents a riser;
14 represents a stripping zone;
15 represents a gas-solid rapid separation zone;
16 represents a disengaging zone;
17 represents a gas outlet;
18 represents a gas-solid cyclone separator;
19 represents a sloped tube for the catalyst to be regenerated; and
20 represents a separation section;
21 represents a catalyst regenerator.

Figure 1:
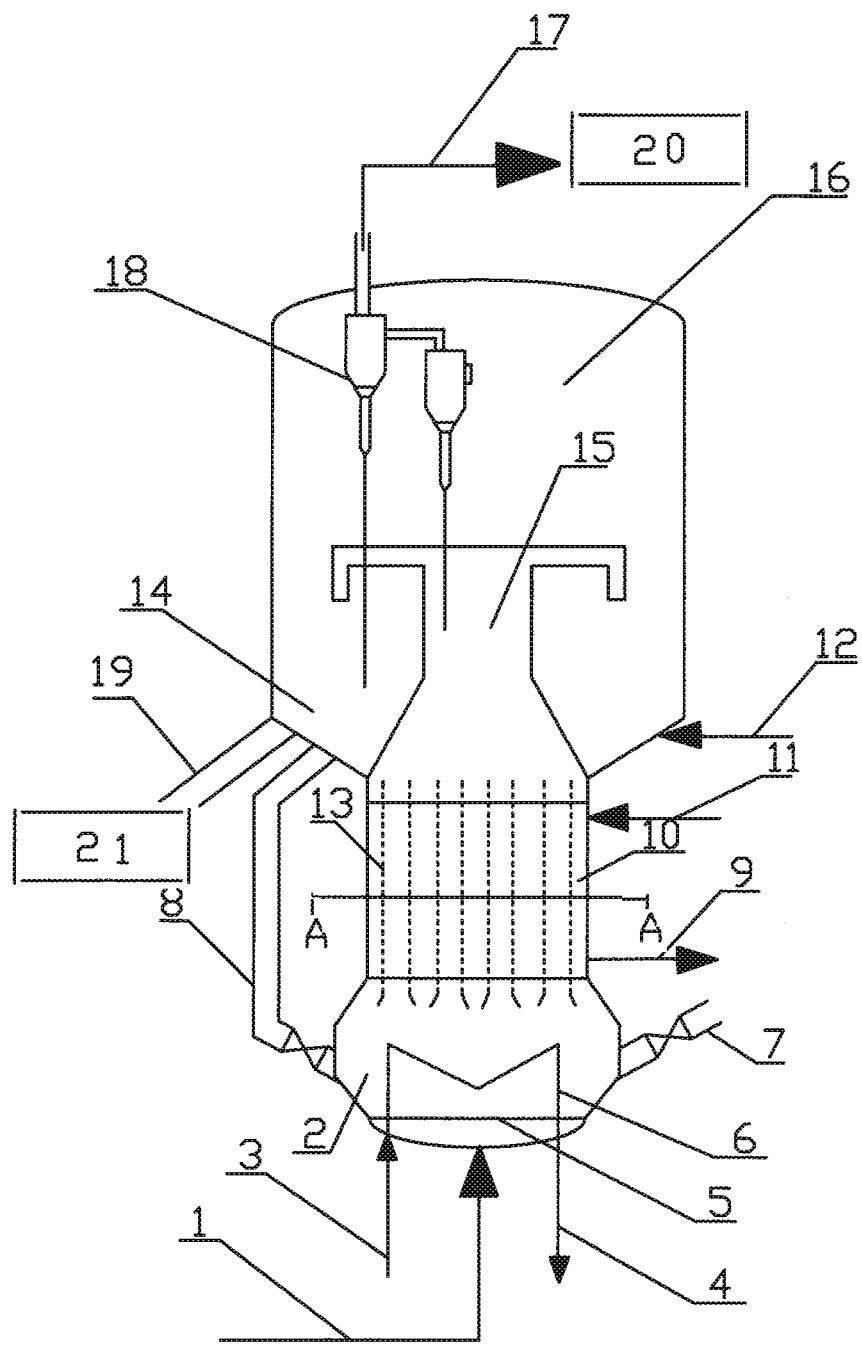
FIG. 1 is a schematic view of a reaction device used in a process according to one embodiment of the present disclosure.
Figure 2:
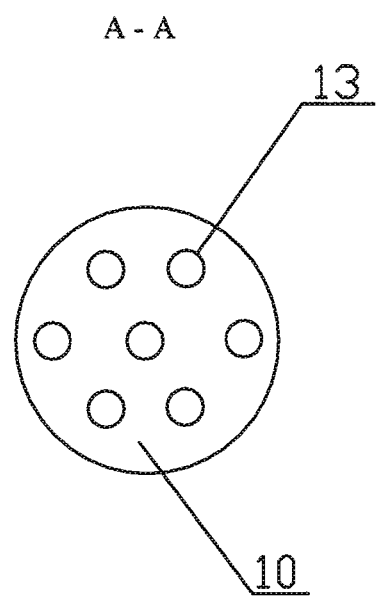
FIG. 2 is a cross-sectional view taken along a plane defined by line A-A in FIG. 1.

In an embodiment of the present disclosure shown in FIG. 1, a feedstock 1 e.g., mainly methanol, enters a pre-reaction zone 2 via a pipeline to contact a catalyst comprising at least one silicon-aluminophosphate molecular sieve. A thus-generated gas-phase stream and the catalyst enter at least one riser 13, and the gas-phase stream and the catalyst pass through an outlet of the riser 13 and then enter a gas-solid rapid separation zone 15. In the gas-solid rapid separation zone 15, the gas-phase stream and the catalyst are separated from one another. The separated gas-phase stream passes through a gas-solid cyclone separator 18 and then passes through a gas outlet 17 and enters a separation section 20. A first portion of the separated catalyst returns to the pre-reaction zone 2 via a recirculation tube 8, and a second portion of the separated catalyst passes through a sloped tube 19 before being regenerated in a regenerator. A cooling coiled tube 6, which includes an inlet 3 and outlet 4 for a second heat exchange medium, is disposed in the pre-reaction zone 2. The at least one riser 13 passes through a heat exchange zone 10, which includes an inlet 11 and an outlet 9 for a first heat exchange medium.

The following representative examples are used to further elucidate the present disclosure, but the present disclosure is not limited to these representative examples.

EXAMPLES

Example 1

In a reaction device as shown in FIG. 1, the catalyst was SAPO-34; the purity of the methanol in the feedstock was 99.5%; the pre-reaction zone 2 contained a dense-phase fluidized bed. The reaction conditions of the pre-reaction zone 2 were: a gauge pressure of 0.01 MPa; an average temperature of 350° C.; the average carbon deposit weight fraction of the catalyst was 1.5%; the gas-phase residence time in the pre-reaction zone 2 was 6 sec. The reaction conditions of the at least one riser 13 were: a gauge pressure of 0.01 MPa; an average temperature of 420° C.; the gas-phase residence time in the at least one riser 13 was 2 sec; the gas-phase residence time in the gas-solid rapid separation zone 15 was 3 sec. The portion of the at least one riser 13 in the heat exchange zone 10 exchanged heat with the first heat exchange medium in an indirect heat exchange manner, and the first heat exchange medium was water. The gas-solid rapid separation zone 15 was within a disengaging zone 16, and the upper portion of the disengaging zone 16 was arranged with a gas-solid cyclone separator 18 for further gas-solid separation. The heat released in the pre-reaction zone 2 was removed by a cooling manner; the internal cooling coiled tube 6 was disposed in the re-reaction zone 2 to exchange heat with the second heat exchange medium; the second heat exchange medium was water. 60% of the at least one riser 13 was within the heat exchange zone 10; there was one riser 13, and the height of the riser 13 was 10 m. 80% of the separated catalyst was returned to the pre-reaction zone 2 and 20% was regenerated in the regenerator. The product gas was analyzed by a gas-phase chromatograph. The yield of light olefin carbon radicals was 81.73% by weight.

Example 2

The conditions and steps described in Example 1 were followed, with the only change of the catalyst type being SAPO-18. The yield of light olefin carbon radicals was 80.41% by weight.

Example 3

The conditions and steps described in Example 1 were followed, except for the parameters below. The pre-reaction zone 2 contained a rapid fluidized bed. The reaction conditions of the pre-reaction zone 2 were: a gauge pressure of 0.01 MPa; an average temperature of 470° C.; the average carbon deposit weight fraction of the catalyst was 4.5%; the gas-phase residence time in the pre-reaction zone 2 was 2 sec. The reaction conditions of the at least one riser 13 were: a gauge pressure of 0.01 MPa; an average temperature of 530° C.; the gas-phase residence time in the at least one riser 13 was 0.4 sec; the gas-phase residence time in the gas-solid rapid separation zone 15 was 1 sec. The portion of the at least one riser 13 in the heat exchange zone 10 exchanged heat with the first heat exchange medium in an indirect heat exchange manner, and the first heat exchange medium was the feedstock comprising methanol. The feedstock methanol was heated to 98° C. 90% of the at least one riser 13 was within the heat exchange zone 10; there were a total number of three risers 13 and the height of each riser 13 was 15 m. 50% of the separated catalyst was returned to the pre-reaction zone 2 and 50% was regenerated in the regenerator. The product gas was analyzed by a gas-phase chromatograph. The yield of light olefin carbon radicals was 84.58% by weight.

Example 4

The conditions and steps described in Example 1 were followed, except for the parameters below. The reaction conditions of the pre-reaction zone 2 were: a gauge pressure of 0.01 MPa; an average temperature of 430° C.; the average carbon deposit weight fraction of the catalyst was 2.8%; the gas-phase residence time in the pre-reaction zone 2 was 3 sec. The reaction conditions of the at least one riser 13 were: a gauge pressure of 0.01 MPa; an average temperature of 500° C.; the gas-phase residence time in the at least one riser 13 was 0.9 sec; the gas-phase residence time in the gas-solid rapid separation zone 15 was 2 sec. The portion of the at least one riser 13 in the heat exchange zone 10 exchanged heat with the first heat exchange medium in an indirect heat exchange manner, and the first heat exchange medium was water. 80% of the at least one riser 13 was within the heat exchange zone 10; there were a total number of seven risers 13 and the height of each riser 13 was 15 m. 60% of the separated catalyst was returned to the pre-reaction zone 2 and 40% was regenerated in the regenerator. The product gas was analyzed by a gas-phase chromatograph. The yield of light olefin carbon radicals was 85.17% by weight.

Example 5

The conditions and steps described in Example 4 were followed, with the only change of the reaction pressure being 0.3 MPa (gauge pressure). The yield of light olefin carbon radicals was 81.69% by weight.

What is claimed is:

1. A process for producing light olefins, comprising the following steps in sequence:
    contacting, in a pre-reaction zone, a feedstock with a catalyst comprising at least one silicon-aluminophosphate molecular sieve to produce a gas-phase stream;
    passing the gas-phase stream and the catalyst into at least one riser;
    passing the gas-phase stream and the catalyst through an outlet of the at least one riser into a gas-solid rapid separation zone to separate therein the gas-phase stream and the catalyst;
    passing the separated gas-phase stream into a separation section;
    returning a first portion of the separated catalyst to the pre-reaction zone, and regenerating a second portion of the separated catalyst in a regenerator;
    wherein an inlet of the at least one riser extends into the pre-reaction zone, about 60% to about 90% of the height of the at least one riser is within a heat exchange zone, the outlet of the at least one riser extends into the gas-solid rapid separation zone, and the average temperature in the at least one riser is higher than the average temperature in the pre-reaction zone.

2. A process for producing light olefins according to claim 1, wherein the at least one silicon-aluminophosphate molecular sieve is chosen from SAPO-5, SAPO-11, SAPO-17, SAPO-18, SAPO-34, SAPO-35, SAPO-44 and SAPO-56.

3. A process for producing light olefins according to claim 2, wherein the at least one silicon-aluminophosphate molecular sieve is SAPO-34.

4. A process for producing light olefins according to claim 1, wherein the pre-reaction zone contains a dense phase and/or rapid fluidized bed.

5. A process for producing light olefins according to claim 1, wherein the feedstock comprises methanol.

6. A process for producing light olefins according to claim 1, wherein the pre-reaction zone comprises the following reaction conditions: a gauge pressure ranging from about 0.01 MPa to about 0.3 MPa; an average temperature ranging from about 350° C. to about 470° C.; an average carbon deposit weight fraction of the catalyst ranging from about 1.5% to about 4.5%; and a gas residence time in the pre-reaction zone ranging from about 2 sec to about 6 sec.

7. A process for producing light olefins according to claim 1, wherein the at least one riser comprises the following reaction conditions: a gauge pressure ranging from about 0.01 to 0.3 MPa; an average temperature ranging from about 420° C. to about 530° C.; and a gas residence time in the at least one riser ranging from about 0.4 sec to about 2 sec.

8. A process for producing light olefins according to claim 1, wherein a gas-phase residence time in the gas-solid rapid separation zone ranges from about 1 sec to about 3 sec.

9. A process for producing light olefins according to claim 1, wherein the portion of the at least one riser in the heat exchange zone exchanges heat with a first heat exchange medium in an indirect heat exchange manner.

10. A process for producing light olefins according to claim 9, wherein the first heat exchange medium comprises water or the feedstock.

11. A process for producing light olefins according to claim 1, wherein the gas-solid rapid separation zone is located within a disengaging zone.

12. A process for producing light olefins according to claim 11, wherein the upper portion of the disengaging zone is arranged with a gas-solid cyclone separator for further gas-solid separation.

13. A process for producing light olefins according to claim 1, wherein heat released in the pre-reaction zone is removed by cooling.

14. A process for producing light olefins according to claim 13, wherein the cooling is accomplished by exchanging heat with a second heat exchange medium in an internal cooling coiled tube.

15. A process for producing light olefins according to claim 14, wherein the second heat exchange medium is water.

16. A process for producing light olefins according to claim 1, wherein the number of the at least one riser comprises at least three risers and the height of each of the risers is at least about 10 m.

17. A process for producing light olefins according to claim 1, wherein the first portion of the separated catalyst, which is returned to the pre-reaction zone, constitutes about 50% to about 80% by weight of the separated catalyst, and the second portion of the separated catalyst, which is regenerated in the regenerator, constitutes about 20% to about 50% by weight of the separated catalyst.

18. A method for preparation of light olefins, comprising conducting the preparation of light olefins in an apparatus for the preparation of light olefins, comprising:
 a pre-reaction zone for contacting a feedstock with a catalyst,
 at least one riser,
 a gas-solid rapid separation zone in flow communication with the at least one riser,
 a separation section, and
 catalyst regenerator;
 wherein an inlet of the at least one riser extends into the pre-reaction zone, about 60% to about 90% of the height of the at least one riser is within a heat exchange zone, an outlet of the at least one riser extends into the gas-solid rapid separation zone, and the average temperature in the at least one riser is higher than the average temperature in the pre-reaction zone.

* * * * *